US009168215B2

(12) United States Patent
Delattre et al.

(10) Patent No.: US 9,168,215 B2
(45) Date of Patent: Oct. 27, 2015

(54) COSMETIC USE OF LACRITIN-TYPE POLYPEPTIDES

(75) Inventors: Caroline Delattre, La Bréle (FR); Dominique Bernard, Vanves (FR); Mark Donovan, Berville (FR)

(73) Assignee: L'OREAL, Paris (FR)

( * ) Notice: Subject to any disclaimer, the term of this patent is extended or adjusted under 35 U.S.C. 154(b) by 49 days.

(21) Appl. No.: 13/383,910

(22) PCT Filed: Jul. 16, 2010

(86) PCT No.: PCT/IB2010/053247
§ 371 (c)(1),
(2), (4) Date: Apr. 2, 2012

(87) PCT Pub. No.: WO2011/007337
PCT Pub. Date: Jan. 20, 2011

(65) Prior Publication Data
US 2012/0190627 A1 Jul. 26, 2012

Related U.S. Application Data

(60) Provisional application No. 61/272,030, filed on Aug. 10, 2009.

(30) Foreign Application Priority Data

Jul. 16, 2009 (FR) ..................................... 09 54929

(51) Int. Cl.
*G01N 33/68* (2006.01)
*A61K 8/64* (2006.01)
*A61Q 5/00* (2006.01)
*A61Q 7/00* (2006.01)
*A61Q 17/00* (2006.01)
*A61Q 19/00* (2006.01)
*A61Q 19/08* (2006.01)

(52) U.S. Cl.
CPC . *A61K 8/64* (2013.01); *A61Q 5/006* (2013.01); *A61Q 7/00* (2013.01); *A61Q 17/005* (2013.01); *A61Q 19/007* (2013.01); *A61Q 19/008* (2013.01); *A61Q 19/08* (2013.01); *G01N 33/6881* (2013.01); *G01N 2333/70596* (2013.01); *G01N 2500/04* (2013.01); *G01N 2500/10* (2013.01)

(58) Field of Classification Search
CPC ..... A61K 8/64; A61Q 17/005; A61Q 19/007; A61Q 19/008; A61Q 19/08; A61Q 5/006; A61Q 7/00; G01N 2333/70596; G01N 2500/04; G01N 2500/10
See application file for complete search history.

(56) References Cited

U.S. PATENT DOCUMENTS

| 7,207,522 B2 | 4/2007 | Parrott et al. | |
| 2004/0081984 A1* | 4/2004 | Laurie et al. | 435/6 |
| 2006/0088852 A1* | 4/2006 | Petersohn et al. | 435/6 |
| 2007/0167372 A1 | 7/2007 | Laurie et al. | |
| 2009/0060962 A1 | 3/2009 | Castiel et al. | |
| 2010/0183572 A1 | 7/2010 | Nakajima et al. | |

FOREIGN PATENT DOCUMENTS

| DE | 102 60 928 A1 | 7/2004 |
| EP | 1 236 463 A1 | 9/2002 |
| EP | 1 766 768 | 3/2007 |
| EP | 2 033 628 A2 | 3/2009 |
| FR | 2 667 778 | 4/1992 |
| FR | 2 905 856 A1 | 3/2008 |
| JP | 2000 264811 A | 9/2000 |
| WO | WO 2004/059001 | 7/2004 |
| WO | WO 2005/119899 | 12/2005 |
| WO | WO 2006/129867 | 12/2006 |
| WO | WO 2007/058383 | 5/2007 |
| WO | WO 2008/033477 | 3/2008 |
| WO | WO 2008/105454 | 9/2008 |
| WO | WO 2009/053564 A2 | 4/2009 |

OTHER PUBLICATIONS

Latterich et al. (European Journal of Cancer, vol. 44:2737-2741 (Nov. 1, 2008).*
NP_444513.1, NCBI, Reference Sequence NP_444513.1, attached as pdf, also available at http://www.ncbi.nlm.nih.gov/protein/NP_444513.1 (last visited Sep. 25, 2014).*
Kyte et al., J. Mol. Biol., 1982, 157:105.
Ma et al., J. Cell Biol., 2006, vol. 174(7):1097-1106.
Mehul et al., J. Biol. Chem., 2000, 275(17):12841-7.
Nakajima et al., Exp. Eye Res., 2007, 85(15):652-658.
Sanghi et al., J. Mol. Biol., 2001, 310(29):127-139.
Wiese et al., Proteomics, 2007, 7:340.
Zieske, J. Exp. Bot., 2006, 57:1501.
Partial English language translation of Preliminary Search Report and Written Opinion for French Priority Application No. 0954929 dated Apr. 20, 2010, 8 pages.
McKnown et al., *Exp. Eye Res.*, May 2009, p. 1-25.
Paragh et al., Exp. Dermatology, vol. 17, issue 12, Dec. 2008, abstract.
Preliminary Search Report and Written Opinion for French Priority Application No. 0954929 dated Apr. 20, 2010.

* cited by examiner

Primary Examiner — Jeffrey E Russel
(74) Attorney, Agent, or Firm — Jones Robb, PLLC

(57) ABSTRACT

The present invention is directed to the use, in particular cosmetic use, of an effective amount of at least one lacritin-type polypeptide, of an analogue thereof or of a fragment thereof, of at least one nucleic acid sequence encoding this polypeptide, or of at least one agent that modulates the activity, the stability or the expression of this polypeptide, or its interaction with syndecan-1, as an agent useful for the care of the skin and of appendages thereof.

2 Claims, 2 Drawing Sheets

SEQ ID NO: 1 atgaaatttaccactctcctcttcttggcagctgtagcagggccctggtctatgctgaagatgcctcctctgactcgacgggtgctg
atcctgcccaggaagctgggacctctaagcctaatgaagagatctcaggtccagcagaaccagcttcacccccagagacaacca
caacagcccaggagacttcggcggcagcagttcaggggacagccaaggtcacctcaagcaggcaggaactaaaccccctgaa
atccatagtggagaaaagtatcttactaacagaacaagcccttgcaaaagcaggaaaaggaatgcacggaggcgtgccaggtg
gaaaacaattcatcgaaaatggaagtgaatttgcacaaaaattactgaagaaattcagtctattaaaaccatgggcatga

SEQ ID NO: 2 gaagatgcctcctctgactcgacgggtgctgatcctgcccaggaagctgggacctctaagcctaatgaagagatctcaggtccag
cagaaccagcttcacccccagagacaaccacaacagcccaggagacttcggcggcagcagttcaggggacagccaaggtca
cctcaagcaggcaggaactaaaccccctgaaatccatagtggagaaaagtatcttactaacagaacaagcccttgcaaaagcag
gaaaaggaatgcacggaggcgtgccaggtggaaaacaattcatcgaaaatggaagtgaatttgcacaaaaattactgaagaaatt
cagtctattaaaaccatgggcatga

SEQ ID NO: 3 atgaaatttaccactctcctcttcttggcagctgtagcagggccctggtctatgct

FIGURE 1

SEQ ID NO: 4

MKFTTLLFLAAVAGALVYAEDASSDSTGADPAQEAGTSKPNEEISGPAEPASPPET
TTTAQETSAAAVQGTAKVTSSRQELNPLKSIVEKSILLTEQALAKAGKGMHGGVP
GGKQFIENGSEFAQKLLKKFSLLKPWA

SEQ ID NO: 5

EDASSDSTGADPAQEAGTSKPNEEISGPAEPASPPETTTTAQETSAAAVQGTAKVT
SSRQELNPLKSIVEKSILLTEQALAKAGKGMHGGVPGGKQFIENGSEFAQKLLKKF
SLLKPWA

SEQ ID NO: 6

MKFTTLLFLAAVAGALVYA

SEQ ID NO: 7

SILLTEQALAK

SEQ ID NO: 8

QFIENGSEFAQK

SEQ ID NO: 9

KFSLLKPWA

SEQ ID NO: 10

GKQFIENGSEFAQKLLKKFSL

FIGURE 2

COSMETIC USE OF LACRITIN-TYPE POLYPEPTIDES

This is a national stage application of PCT/IB2010/053247, filed internationally on Jul. 16, 2010, which claims priority to French Application No. 0954929, filed on Jul. 16, 2009, and U.S. Provisional Patent Application No. 61/272,030, filed on Aug. 10, 2009.

The present invention relates to the field of protein markers for the skin and the appendages thereof and to the use of said markers as targets or as cosmetic or therapeutic active agents for the prevention and/or treatment of disorders.

In particular, the subject of the present invention is the use, in particular cosmetic or therapeutic use, of an effective amount of at least one lacritin-type polypeptide, of an analogue thereof or of a fragment thereof, of at least one nucleic acid sequence encoding this polypeptide, or of at least one agent that modulates the activity, the stability or the expression of this polypeptide, or of the interaction thereof with syndecan-1, as an agent useful for the care of the skin and of appendages thereof. The invention also relates to the use of at least one lacritin-type polypeptide, of an analogue thereof or of a fragment thereof, or of at least one nucleic acid sequence encoding this polypeptide, as a tool for in vitro or ex vivo characterization of a condition of the skin.

The epidermis, which is the superficial part of the skin, is a tissue of which the cells are joined to and interlinked with one another and lie on a basal membrane. It forms an external covering comprising sebaceous or sweat glands. More specifically, the epidermis is a structure of which the homeostasis results from the implementation of a finely regulated collection of intracellular and extracellular signals acting at all the steps of cell proliferation, migration and differentiation, and also the steps of synthesis of the various extracellular matrix components. These signals can in particular result from the action of factors produced by keratinocytes.

The epidermis is conventionally divided up into a basal layer of keratinocytes containing, in particular, skin stem cells and constituting the germinative layer of the epidermis, a "spiny" layer constituted of several layers of polyhedral cells placed on the basal layer, a "granular" layer comprising one to three layers said to be of flattened cells containing distinct cytoplasmic inclusions, keratohyalin granules and, finally, a set of upper layers, called horny layer, or stratum corneum, constituted of keratinocytes at the terminal stage of their differentiation, called corneocytes.

The stratum corneum, which is the outermost part of the skin and which performs the function of a barrier between the organism and the environment, and the hair shaft, which is the emerging part of the hair follicle which constitutes the head of hair, both represent the result of the keratinocyte differentiation process. Epidermal differentiation follows a process of maturation in which keratinocytes of the basal layer differentiate and migrate so as to result in the formation of corneocytes, which are completely keratinized dead cells. This differentiation is the result of perfectly coordinated phenomena which will result in the thickness of the epidermis being kept constant and thus ensure the homeostasis of the epidermis.

Many skin disorders or pathological skin conditions can result from a dysfunction of epidermal homeostasis, and in particular of the proliferation and/or renewal of the terminal cells of the skin and/or of the hair follicle, and in particular of the keratinocytes.

It is by this time known that these dysfunctions may in particular be associated with different modulation of the expression and/or of the biological activity of certain proteins expressed in the stratum corneum.

Surprisingly, the inventors have observed, for the first time, the expression of lacritin, and in particular of three peptides derived from lacritin, represented by the sequences SEQ ID NO: 7, SEQ ID NO: 8 and SEQ ID NO: 9, at the level of the skin, and in particular a decrease in its expression, and in particular in the expression of the abovementioned three peptides, in aged and/or dry skin. Thus, against all expectations, lacritin proves to be a marker for the physiological condition of the skin, in particular from the viewpoint of ageing and/or dryness of the skin.

In addition, it has also been observed that the proteoglycan syndecan-1 and also heparanase 1, as described hereinafter, which are both involved in the biological activity of lacritin described in the eyes, are strongly expressed in the epidermis and the hair follicle.

It has also been observed by the inventors that the administration of an active agent composed of a lysate of probiotic bacteria, in particular of the species *Bifidobacterium longum*, and of a phytosphingosine-salicylate derivative advantageously makes it possible to restore the expression of lacritin in aged and/or dry skin.

Consequently, according to one of its first aspects, the subject of the present invention is a cosmetic, or even non-therapeutic, use of an effective amount of at least one polypeptide of amino acid sequence represented by SEQ ID NO: 4, an analogue thereof or a fragment thereof, of at least one nucleic acid sequence encoding this polypeptide, or of at least one agent that modulates the activity, the stability or the expression of this polypeptide, or its interaction with syndecan-1, as an agent useful for the care of the skin and of appendages thereof.

Lacritin is a glycoprotein comprising, in its preprotein form, 138 amino acids and having a molecular weight of approximately 14.2 kDa for the nonglycosylated polypeptide.

Lacritin is known to be expressed in the secretory granules of the acinar cells of lacrimal and saliva glands. The properties of lacritin have been widely described in terms of the eye and the epithelial cells of the cornea, and it has been proposed in various ophthalmic treatments, for instance in WO 2005/119899, WO 2008/105454, US 2007/0167372, U.S. Pat. No. 7,207,522 and EP 1 766 768.

Lacritin has a mitogen activity on the epithelial cells of the cornea, and has also been characterized as promoting tear secretion. A decrease in lacritin expression has been observed in patients suffering from blepharitis, an inflammation of the cutaneous covering of the eyelids, or, in certain cases, termed "dry eyes" (Sanghi et al., J. Mol. Biol., 2001, 310(29):127-139; Nakajima et al., Exp. Eye Res., 2007, 85(15):652-658; McKnown et al., Exp. Eye Res., 2008: 1-11).

At the ophthalmic level, this polypeptide also has an antimicrobial activity (WO 2008/033477 or WO 2006/129867) and promotes lipid secretions (WO 2007/058383).

The activity of lacritin appears in particular to require the association of its C-terminal end with the N-terminal part of the proteoglycan syndecan-1 (SDC1) deglycosylated beforehand with heparanase-1, an enzyme intended to degrade heparan sulphate.

For the purpose of the present invention, the term "skin" also denotes the scalp. With regard to the skin, the term "appendages" is more particularly understood to denote the nails, body hairs or the hair.

The term "care of the skin and of appendages thereof" is intended to mean more particularly stimulating proliferation and/or renewal of the terminal cells of the skin and/or the hair follicle, and even more particularly preventing and/or treating a skin and/or hair disorder.

In particular, the present invention is directed towards preventing and/or treating the cutaneous signs of ageing, in particular for preventing and/or treating thinning of an epidermis and/or loss of firmness, of elasticity, of density and/or tonicity of an epidermis and/or the formation of wrinkles and fine lines, towards preventing and/or treating the cutaneous signs of dryness, in particular preventing and/or treating dehydration of the skin, towards preventing and/or treating skin disorders due to an imbalance in the barrier properties of the skin, in particular for stimulating the cutaneous antimicrobial defences, and in particular for the treatment and/or prevention of acne and/or of dandruff, towards regulating sweating and/or the sebaceous secretions of the skin, in particular for preventing and/or treating skin disorders associated, respectively, with hyperhidrosis or hypohidrosis, or else with hyperseborrhoea or hyposeborrhoea, and towards stimulating the growth of body hairs and of the hair.

The term "regulating" is intended to mean, with regard to a given effect, the action of stimulating or inhibiting this effect so as to confer a physiological intensity thereon.

For the purpose of the invention, the term "cosmetic use" is intended to denote a use intended, mainly, to provide an aesthetic and/or comfort effect.

According to another of its aspects, the subject of the present invention is also the use of an effective amount of at least one polypeptide of amino acid sequence represented by SEQ ID NO: 4, an analogue thereof or a fragment thereof, of at least one nucleic acid sequence encoding this polypeptide, or of at least one agent that modulates the activity, the stability or the expression of this polypeptide, or of its interaction with syndecan-1, for the preparation of a therapeutic composition for the care of the skin and of appendages thereof.

For the purposes of the invention, the term "therapeutic composition" is intended to mean a composition intended to provide a prophylactic or curative effect with regard to epidermal disorders, known to reflect a pathological condition.

For the purpose of the present invention, the expression "effective amount" is intended to mean the minimum amount required for the observation of the expected effect, namely a cosmetic effect or a therapeutic effect, it being understood that the effective amounts required for obtaining a cosmetic effect or a therapeutic effect, may, as appropriate, be identical or different.

For the purpose of the present invention, the term "preventing" or "prophylaxis" is intended to mean the total or partial suppression of a risk of occurrence of an event or a phenomenon. When the suppression is partial, the risk of occurrence of the given event or phenomenon is reduced compared with said risk before the implementation of the present invention.

According to another aspect, the present invention also relates to the use of at least one polypeptide or of at least one nucleic acid sequence encoding said polypeptide, as a tool for screening for biological or chemical compounds or for physical treatments capable of modulating the biological activity, the stability and/or the expression of said polypeptide or of said nucleic acid sequence, or the interaction of said polypeptide with syndecan-1.

The screened biological or chemical compounds or physical treatments may be advantageously used for caring for the skin and its appendages.

In particular, the present invention relates to a method for screening for biological or chemical compounds or for physical treatments capable of modulating the expression of a polypeptide according to the invention, or of a nucleic acid sequence encoding said polypeptide, comprising at least the steps consisting in:

a) bringing at least one isolated cell capable of expressing said polypeptide or said nucleic acid sequence into contact with at least one chemical or biological compound to be tested, or exposing said isolated cell to the physical treatment to be tested, under conditions suitable for the expression of said polypeptide or of said nucleic acid sequence, b) carrying out a qualitative or quantitative measurement of said polypeptide or of said nucleic acid sequence, and c) comparing said measurement to a reference measurement.

The screened biological or chemical compounds or physical treatments may be advantageously used for caring for the skin and its appendages.

A "reference measurement", with regard to a given parameter, is a qualitative or quantitative measurement of this parameter carried out under controlled conditions, namely in the absence of the factor of which the effect on the parameter is evaluated.

For example, for a method for screening for a biological or chemical compound or for a physical treatment, a "reference measurement" can be obtained by carrying out a measurement of the polypeptide, or of the nucleic acid sequence encoding the polypeptide, which is qualitative, namely an absence or a presence of said polypeptide or of said nucleic acid sequence, or which is quantitative, namely a content of the polypeptide or of the nucleic acid sequence, in the absence of the compound or of the physical treatment tested.

In the case of a method for characterizing a condition of the skin, as detailed hereinafter, a "reference measurement" can be obtained by carrying out a qualitative or quantitative measurement of the polypeptide, or of the nucleic acid sequence encoding the polypeptide, in a skin sample that is distinct from that which is the subject of the characterization, and which can be described as normal skin with regard to the skin evaluated, i.e. which is satisfactory from the physiological point of view, like, for example, young skin devoid of signs of dryness of the skin.

Preferably, a reference measurement is a statistic measurement, i.e. a measurement which has been repeated on various samples so as to obtain a mean.

The reference measurement can be carried out in parallel or sequentially to the test measurement, which is, for example, the measurement defined in step b) of the method described above. It can also be a "historical" measurement, i.e. a measurement carried out prior to the test measurement, and stored, for example in a database, with a view to subsequent use.

The comparison of the test measurement to the reference measurement, and the observation of a deviation or of a lack of deviation between the two measurements, makes it possible to extract information regarding the effect of the factor evaluated, for example the effect of a biological or chemical compound or of a physical treatment on lacritin expression, or with regard to the aged or dry nature of the skin.

The invention also relates to a method for screening for biological or chemical compounds capable of modulating the biological activity of a polypeptide in accordance with the invention, comprising at least the steps consisting in:

a) bringing at least one isolated polypeptide in accordance with the invention into contact with at least one chemical or biological compound to be tested, under conditions suitable for the manifestation of the biological activity of said polypeptide, b) carrying out a qualitative or quantitative measurement of said biological activity, and c) comparing said measurement to a reference measurement.

The screened biological or chemical compounds may be advantageously used for caring for the skin and its appendages.

According to yet another of its aspects, the present invention also relates to the use of at least one polypeptide in accordance with the invention or of at least one nucleic acid sequence encoding said polypeptide, as a tool for in vitro or ex viva characterization of a condition of the skin.

More specifically, according to another of its aspects, the present invention relates to a method for characterizing a condition of the skin, comprising at least the steps consisting in:

a) carrying out, in an isolated sample of said skin, a qualitative or quantitative measurement of a polypeptide in accordance with the invention, or of a nucleic acid sequence encoding said polypeptide, and b) comparing said measurement carried out in step a) to a reference measurement.

As emerges from the description which follows, the methods according to the invention are particularly advantageous insofar as the implementation thereof does not require an invasive procedure. The methods of the invention can be carried out in vitro or ex vivo.

This is because the localization, by the inventors, of the new biomarker for aged skin and/or for dry skin represented by lacritin, in the stratum corneum, makes it possible to quantitatively or qualitatively characterize the expression of this protein by simple topical sampling. The sampling method may, for example, be a stripping technique consisting in applying a portion of adhesive tape to the epidermis under consideration. When this adhesive tape is detached, a fraction of the surface of the skin is sampled. After protein extraction, it is then analysed by conventional methods, such as ELISA enzyme immunoassay or Western blotting analysis, or more particularly by means of the iTRAQ differential proteomic method as defined hereinafter.

According to yet another of its aspects, the present invention is directed towards the use of at least one polypeptide in accordance with the invention; or of at least one nucleic acid sequence encoding said polypeptide, for characterizing the effectiveness of a cosmetic treatment for the care of the skin and of appendages thereof, in particular for characterizing the effectiveness of a treatment for a skin disorder as defined above.

According to another of its aspects, the present invention is directed towards the use of an effective amount of at least one polypeptide in accordance with the invention or of at least one nucleic acid sequence encoding said polypeptide, or of at least one agent that modulates the activity, the stability or the expression of said polypeptide or of said nucleic acid sequence, or the interaction of said polypeptide with syndecan-1, for preparing and/or improving a pluristratified epithelial cell model, in particular a reconstructed skin model.

Conditions of the Skin

The conditions of the skin or of the epidermis to which the invention relates are a matter for epidermises exhibiting signs resulting from disorders of the proliferation and/or renewal of the terminal cells of the skin and/or of the hair follicle.

These conditions of the skin may be a matter for a cosmetic and/or therapeutic use, and in particular for a cosmetic and/or therapeutic treatment and/or prevention method.

More particularly, the conditions of the skin to which the invention relates may be as described hereinafter.

Cutaneous Signs of Ageing

The term "cutaneous signs of ageing" is intended to mean any modifications of the external appearance of the skin due to ageing, whether it is chronobiological and/or photoinduced, for instance wrinkles and fine lines, wizened skin, lack of elasticity and/or of tonicity of the skin, thinning of the dermis and/or degradation of the collagen fibres, thereby leading to the appearance of flaccid and wrinkled skin. The term is also intended to mean all the internal modifications of the skin which do not systematically result in a modified external appearance, for instance all the internal degradations of the skin, in particular of the elastin fibres, or elastic fibres, subsequent to exposure to ultraviolet radiation.

In particular, the cutaneous signs of ageing towards which the invention is directed concern all the modifications of the external appearance of the skin due to ageing, whether it is chronological and/or photoinduced, for example thinning of an epidermis and/or a loss of firmness, of elasticity, of density and/or of tonicity of an epidermis and/or the formation of wrinkles and fine lines.

Cutaneous Signs of Dryness

The term "cutaneous signs of dryness" is intended to mean all the modifications of the external appearance of the skin due to dehydration of the epidermis.

Dry skin seems rough to the touch and seems covered with squamae and manifests itself mostly through a feeling of tautness and/or of tension.

The origin of dryness of the skin may be of constitutional or acquired type.

In the case of constitutional dry skin, two categories can be distinguished: pathological skin and nonpathological skin.

Pathological constitutional dry skin is essentially represented by atopic dermatitis and ichthyosis. It is virtually independent of the external conditions, and arises from known or unknown genetic modifications.

In the case of nonpathological constitutional dry skin, the severity of the condition of dryness may, for its part, depend on external factors. Senile skin, in particular characterized by a general decrease in skin metabolism with age, fragile skin, which can be characterized by skin that is very sensitive to external factors and often accompanied by erythema and rosacea, and xerose vulgaris, of probable genetic origin and mainly manifested on the face, the limbs and the back of the hands, are included in this skin category.

Irrespective of the origin, skin, suffering from skin dryness generally presents the following signs, namely a rough and flaky feel, and also decreased suppleness and elasticity.

Dry skin, also known as "xerosis", may appear at any age, and may be unconnected to a pathological condition. It will be referred to in this case as "acquired" dryness.

Although no study has demonstrated dryness having an effect on the origin and formation of wrinkles and fine lines, which are essentially attributable to ageing, in visual terms, a dry skin makes wrinkles and fine lines more apparent.

Moreover, from a sensory viewpoint, skin dryness is characterized by a feeling of tautness and/or itching. For obvious reasons, these manifestations are not only a source of discomfort, or even of pain, but are also inaesthetic.

Skin Barrier Disorders

The barrier function is mainly provided by the uppermost layer of the epidermis, namely the horny layer, also known as the stratum corneum. It constitutes a barrier against external attacks, in particular chemical, mechanical or infectious attacks, and, in this respect, a certain number of defence reactions against environmental factors, such as, for example, the climate, ultraviolet rays, or tobacco and/or xenobiotics, for instance microorganisms, occur therein.

An impairment of the skin barrier can occur in the presence of external attacks such as irritants, for instance detergents, acids, bases, oxidants, reducing agents, concentrated solvents, toxic gases or fumes, mechanical stresses, for instance rubbing, impacts, abrasion, tearing of the surface, projection of dust or particles, shaving or depilation, heat or climatic imbalances, for example cold, dryness, radiation or xenobiotics, in particular undesirable microorganisms or allergens, or of internal attacks such as psychological stress.

The skin barrier disorders can in particular result in skin discomfort, sensory phenomena and in particular unpleasant phenomena, in particular tingling, tautness, heating and itching.

Scalp Disorders

Dandruff conditions are chronic, frequent, recurring conditions that are socially incapacitating owing to their obvious unattractive nature. Many factors can amplify these phenomena and result in the appearance of additional disorders, such as inflammatory conditions of the scalp generating itching sensations or pruritus, resulting in scratching behaviour which amplifies the dandruff appearance phenomenon. Dandruff conditions of the scalp may be of oily type or of dry type.

Dry dandruff conditions of the scalp are more common and are amplified during skin hydration disorders, and in particular during considerable dryness of the epidermis of the scalp. Dry dandruff conditions reflect xerosis of the scalp, where appropriate associated with an excessively rapid renewal of the stratum corneum thereof. Dry dandruff is generally in the form of small white or grey pieces and becomes distributed over the scalp and the clothing, generating an unattractive visual effect.

Moreover, excessive sebum secretion promotes the appearance of an oily dandruff condition of the scalp, or oily dandruff. It has a tendency to be more readily pruritic. Oily dandruff is one of the forms of seborrhoeic dermatitis. Individuals who suffer therefrom have an erythematous scalp covered with large, oily yellow squamae that accumulate to form packets. They have a pruritic scalp, and often have burning sensations on the affected areas.

In addition, a scalp exhibiting excessive dryness or excessive sebum secretion can show pruritus and/or an inflammation of the epidermis.

Hair Disorders

Hair growth and hair renewal are mainly determined by the activity of the hair follicles and of their surrounding matrix. Their activity is cyclical and comprises essentially 3 phases, namely the anagenic phase, the catagenic phase and the telogenic phase. Following the terminal or telogenic phase, which lasts a few months, the hairs fall out and another cycle begins again. The head of hair is thus under constant renewal and, out of the approximately 150 000 hairs that make up a head of hair, at each moment, approximately 10% are at rest and will be replaced within a few months. The natural loss or falling-out of the hair may be estimated, on average, as being a few hundred hairs per day for a normal physiological condition. This process of constant physical renewal undergoes a natural change during ageing; the hairs become finer and their cycles shorter.

On the other hand, in certain types of dermatosis of the scalp with an inflammatory nature, such as, for example, psoriasis or seborrhoeic dermatitis, hair loss can be greatly accentuated and the follicle renewal cycles can be greatly disrupted. In addition, various causes can lead to a substantial, temporary or permanent loss of hair. This may be loss and detrimental alteration of the hair during a pregnancy (post partum), during states of dietary malnutrition or imbalance, or else during states of asthenia or of hormonal dysfunction, as may be the case during or at the end stage of the menopause. It may also be a case of loss or detrimental alteration of the hair related to seasonal phenomena. It may also be a question of alopecia, which is essentially due to disturbances in hair renewal which lead, in a first stage, to acceleration of the frequency of the cycles to the detriment of the quality of the hair, and then of the amount. The term "alopecia" also covers an entire family of afflictions of the hair follicle whose final consequence is the permanent, partial or general loss of the hair. This more particularly involves androgenic alopecia. In a large number of cases, premature hair loss occurs in genetically predisposed individuals; this is then androchronogenetic alopecia; this form of alopecia especially affects men.

Healing Disorders

Correct healing involves cooperation between dermal fibroblasts and epidermal keratinocytes by means of cytokins that promote cell proliferation and migration and synthesis of the extracellular matrix components, making it possible to, in a first stage, fill the scar and then, in a second stage, develop a renewed epidermal barrier function by fine regulation of keratinocyte differentiation.

Lacritin can act positively at these various stages.

Secretory Disorders, in Particular of Sudoriparous and Sebaceous Type

Secretions contribute greatly to the state of hydration of the skin through their provision, at the epidermis surface, of hydrating elements such as, for example, urea, lactates, salts, or lipophilic compounds which oppose water loss. This hydrated state is either desirable, for example in order to combat skin dryness, or is a source of undesired microbial developments responsible for unpleasant odours, in particular underarm odours, and/or of desquamation and barrier function disorders, in particular on the scalp. These secretions and the constituent elements thereof are also largely responsible for the surface hydrolipid film appearance and the modulation of such secretions may be desirable, for example, in order to combat the oily skin appearance.

Lacritin can advantageously regulate these secretions.

Antimicrobial Defence Disorders

The superficial layers of the epidermis constitute a barrier against the penetration of microorganisms. This barrier is not only physical, but also biochemical, and in particular by means of antimicrobial molecules such as antimicrobial peptides. In certain skin disorders such as atopic dermatitis, acne or rosacea, an imbalance in these defences has been implicated. Lacritin, by virtue of its specific antimicrobial properties and/or its ability to regulate the synthesis of molecules with antimicrobial properties, can advantageously correct these disorders.

According to one embodiment, a cosmetic use according to the invention focuses more particularly on the prevention and/or treatment of a condition of the skin chosen from the cutaneous signs of ageing, in particular thinning of an epidermis and/or the loss of firmness, of elasticity, of density and/or of tonicity of an epidermis and/or the formation of wrinkles and fine lines, the cutaneous signs of dryness, in particular dehydration of the skin, skin disorders due to an imbalance in the barrier properties of the skin, in particular in the antimicrobial defences of the skin, and especially to acne and/or to dandruff, sweating or sebaceous secretion disorders, in particular skin disorders associated, respectively, with hyperhidrosis or hypohidrosis, and with hyperseborrhoea or hyposeborrhoea, and disorders of the growth of body hairs and of the hair.

In particular, a cosmetic use according to the invention focuses more particularly on the prevention and/or treatment of a condition of the skin chosen from xerosis, parakeratosis, hyperkeratosis, oily skin, skin odour, a disregulation of sweating or of sebogenesis, alopecia, hirsutism, acne or dry or oily dandruff.

According to one embodiment, a therapeutic or dermatological use according to the invention focuses more particularly on the prevention and/or treatment of a condition of the skin chosen from ichthyosis, rosacea, lichen, seborrhoeic dermatitis, palmoplantar keratoderma, a healing disorder or a skin disorder involving secretion and cell invasion process phenomena, in particular in the context of malignant or benign neoplasias, psoriasis, skin atopy, atopic dermatitis, or alopecia or alopecia greata.

Polypeptide

According to one embodiment, a polypeptide suitable for the invention is a polypeptide of amino acid sequence represented by SEQ ID NO: 4, an analogue thereof, or a fragment thereof.

For the purpose of the present invention, the term "lacritin" is intended to denote, in general, unless otherwise indicated, the sequence SEQ ID NO: 4, optionally having undergone post-translational modifications of glycosylation type on the asparagine residue at position 119, which are optionally capable of modifying its apparent molecular weight or its isoelectric point, and the variants resulting from alternative splicing.

The term "analogue of a polypeptide" is intended to denote any polypeptide exhibiting a sequence identity, in particular with respect to one of the characteristic sequences of said polypeptide, and also a biological activity of the same nature.

The term "characteristic sequence of the polypeptide" is intended to be directed towards, in particular with regard to lacritin, the sequence represented by SEQ ID NO: 4.

This analogue may be a peptidomimetic agent.

The sequence identity can be at least 85%, for example at least 90%, and for example at least 95%. The sequence identity can be determined by visual comparison or by means of a computer tool widely used in the field, such as the BLAST programs available from the National Institutes of Health and used with the default parameters.

An analogue of a polypeptide of the invention can result from modifications derived from mutation or variation in the sequences of the peptides according to the invention, originating either from the deletion or from the insertion of one or more amino acids, or from the substitution of one or more amino acids in the characteristic sequences of a polypeptide according to the invention. Several of these modifications can be combined.

Advantageously, an analogue of a polypeptide of the invention can comprise conservative substitutions relative to the amino acid sequence of the natural polypeptide.

By way of example of mutations that may be considered in the present invention, mention may be made, nonexhaustively, of the replacement of one or more amino acid residues with amino acid residues having a similar hydropathic index, without however substantially affecting the biological properties of the polypeptide. The hydropathic index is an index assigned to amino acids as a function of their hydrophobicity and of their charge (Kyle et al. (1982), J. Mol. Biol., 157: 105).

A polypeptide or analogue that is also covered by the present invention may be a polypeptide having undergone one or more post-translational modification(s).

The term "post-translational modification(s)" is intended to encompass all the modifications that a peptide or a protein is capable of undergoing at the end of its synthesis in a cell, such as, for example, one or more phosphorylation(s), one or more thiolation(s), one or more acetylation(s), one or more glycosylation(s), one or more lipidation(s), such as a farnesylation or a palmitoylation, a structural rearrangement of the type involving the formation of disulphide bridges and/or cleavage within the peptide sequence.

The analogue has, moreover, substantially the same biological activity as the natural polypeptide.

It is, moreover, known that the primary sequence of a polypeptide, i.e. the succession of the amino acids, determines sites specifically recognized by protease-type enzymes, such as trypsin, which, once the recognition of these sites has become effective, will induce cleavage of the polypeptide by proteolysis. This proteolysis results in the generation of various peptides, or proteolytic fragments, of lacritin.

Consequently, the invention also extends to the fragments of lacritin which are derived, where appropriate, from the proteolysis thereof.

For the purpose of the invention, the term "polypeptide fragment" is intended to mean any portion of a polypeptide in accordance with the invention comprising at least 3, preferably at least 8, or even at least 10, and more particularly at least 12 consecutive amino acids of said polypeptide, and a substantially similar biological activity.

As detailed in the examples, the inventors have detected the presence of peptide fragments of lacritin in the human stratum corneum.

Thus, according to one embodiment, a polypeptide suitable for the invention can be a polypeptide of amino acid sequence represented by SEQ ID NO: 5, SEQ ID NO: 6, SEQ ID NO: 7, SEQ ID NO: 8, SEQ ID NO: 9 or SEQ ID NO: 10, an analogue thereof, or a fragment thereof.

Preferably, a polypeptide suitable for the invention can be a polypeptide of amino acid sequence represented by SEQ ID NO: 7, SEQ ID NO: 8, SEQ ID NO: 9 or SEQ ID NO: 10, an analogue thereof or a fragment thereof.

Even more preferably, a polypeptide suitable for the invention can be a polypeptide of amino acid sequence represented by SEQ ID NO: 7, SEQ ID NO: 8 or SEQ ID NO: 9, an analogue thereof or a fragment thereof.

According to another embodiment, a polypeptide suitable for the invention can also be a natural or synthetic polypeptide, where appropriate capable of being obtained after enzymatic or chemical lysis of lacritin or by chemical or biological synthesis or by extraction from a biological tissue, for instance the skin, expressing this polypeptide naturally or after transfection thereof, and also the various post-translational forms of said polypeptide, or else any natural or synthetic polypeptide of which the sequence completely or partially (entirely or partly) comprises an amino acid sequence mentioned above, for example the variants and the analogues.

Those skilled in the art can obtain a polypeptide in accordance with the invention by means of recombinant DNA-based methods, for instance those described in the manual "Molecular Cloning—A Laboratory Manual" (2nd edition), Sambrook et al., 1989, Vol. 1411, Coldspring Harbor Laboratory, Coldspring Harbor Press, NY (Sambrook).

Advantageously, a polypeptide of the invention may be encoded by a nucleic acid sequence represented by SEQ ID NO: 1, SEQ ID NO: 2 or SEQ ID NO: 3, an analogue thereof or a fragment thereof.

According to another embodiment, a polypeptide suitable for the implementation of the invention may also be a polypeptide as defined above, fused with another polypeptide, a hydrophilic or hydrophobic targeting agent, a bioconversion precursor, or a luminescent, radioactive or colorimetric labelling agent.

In a nonlimiting manner, mention may be made, as an example of compounds that can be coupled with a polypeptide in accordance with the invention, of fluorescent proteins such as Green Fluorescent Protein, fluorescent chemical compounds such as rhodamine, fluorescein or Texas Red®, phosphorescent compounds, radioactive elements, such as $^3$H, $^{14}$C, $^{35}$S, $^{121}$I or $^{125}$I, or colorimetric labelling agents such as chromogenic substrates sensitive to the action of galactosidase, of peroxidase, of chloramphenicol acetyltransferase, of luciferase or of alkaline phosphatase.

Depending on the nature of the compounds that can be coupled with a polypeptide in accordance with the invention, the coupling may be performed by chemical methods, in particular by means of reactive chemical functions, or by molecular biology methods known to those skilled in the art.

Nucleic Acids

According to one embodiment, the present invention also relates to nucleic acid sequences encoding a polypeptide of the invention and to the employment thereof in the various uses and methods in accordance with the invention.

Thus, the present invention also relates to the use of a nucleic acid sequence, in particular deoxyribonucleic acid sequence or ribonucleic acid sequence, represented by SEQ ID NO: 1, an analogue thereof or a fragment thereof.

For the purpose of the present invention, the term "nucleic acid sequence fragment" is intended to mean a nucleic acid sequence encoding a polypeptide in accordance with the invention, especially as defined above, and in particular a nucleic acid sequence represented by SEQ ID NO: 2 or SEQ ID NO: 3, or an analogue thereof.

The term "analogue of a nucleic acid sequence" is intended to denote any nucleic acid sequence possibly resulting from the degeneracy of the nucleic acid code, and encoding a polypeptide in accordance with the invention, in particular as defined above.

The nucleic acid sequences may be derived from all possible origins, i.e. either animal origin, in particular mammalian origin and even more particularly human origin, or plant origin, or microbial origin, for instance viruses, phages or bacteria, inter alia, or else fungal origin, without prejudice regarding whether or not they are naturally present in said organism of origin.

According to one embodiment, the invention also relates to the isolated and purified nucleic acid sequences encoding the polypeptides under consideration according to the invention, and also to the analogues and fragments thereof.

A nucleic acid sequence in accordance with the invention may comprise a sense, antisense, or interfering sequence corresponding to a sequence encoding a polypeptide in accordance with the invention.

A subject of the invention is also nucleic acid sequences, in particular ribonucleic or deoxyribonucleic acid sequences, comprising a sense or antisense sequence, in particular small interfering RNA (siRNA), corresponding at least to a sequence encoding a polypeptide of the invention or a nucleic acid sequence represented by SEQ ID NO: 1, SEQ ID NO: 2 or SEQ ID NO: 3, an analogue thereof or a fragment thereof.

Screening

Screening Method

According to one of its aspects, the present invention relates to the use of at least one polypeptide in accordance with the invention, or of at least one nucleic acid sequence encoding said polypeptide, as a tool for screening for biological or chemical compounds or for physical treatments capable of modulating the biological activity, the stability and/or the expression of said polypeptide or of said nucleic acid sequence, or the interaction of said polypeptide with syndecan-1.

The screened biological or chemical compounds or physical treatments may be advantageously used for caring for the skin and its appendages.

A method for screening for biological or chemical compounds or for physical treatments capable of modulating the expression of a polypeptide in accordance with the invention, or of a nucleic acid sequence encoding said polypeptide, can comprise at least the steps consisting in:

a) bringing at least one isolated cell capable of expressing said polypeptide or said nucleic acid sequence into contact with at least one chemical or biological compound to be tested, or exposing said isolated cell to the physical treatment to be tested, under conditions suitable for the expression of said polypeptide or of said nucleic acid sequence, b) carrying out a qualitative or quantitative measurement of said polypeptide or of said nucleic acid sequence, and c) comparing said measurement to a reference measurement.

A reference measurement can be obtained by repeating steps a) and b) in the absence of biological or chemical compounds, or of physical treatments to be tested.

A nucleic acid sequence suitable for the implementation of a method according to the invention may advantageously be a nucleic acid sequence encoding lacritin, for example of mRNA type.

The qualitative or quantitative measurement of the expression of a nucleic acid sequence can be determined, for example, by means of oligonucleotide probes, using any protocol known to those skilled in the art.

By way of example of methods for detecting nucleic acid sequences, mention may be made of the quantitative (Q-PCR) or nonquantitive polymerase chain reaction (PCR), in the presence or absence of reverse transcriptase (RT-PCR or Q-RT-PCR), of Northern blotting, of the ribonuclease protection assay method, of methods with DNA chips, of methods with transcriptome chips, of methods with oligonucleotide chips, and of in situ hybridization methods.

By way of example of agents suitable for the detection of a nucleic acid sequence, and in particular of mRNA, mention may be made of labelled nucleic acid probes that can hybridize to a nucleic acid sequence in accordance with the invention.

Such a nucleic acid probe can be readily obtained by any method known to those skilled in the art.

Thus, the nucleic acid sequences in accordance with the invention may be used to prepare sense and/or antisense oligonucleotide primers which hybridize, under high stringency conditions, to at least one of the sequences SEQ ID NO: 1, SEQ ID NO: 2 or SEQ ID NO: 3, an analogue thereof or a fragment thereof.

The expression of a nucleic acid sequence may also be determined, indirectly, by determining the expression of the polypeptide encoded by said sequence, by means of any technique known in the field, such as Western blotting, ELISA, the Bradford or Lowry method, or as indicated hereinafter.

The qualitative or quantitative measurement, in particular a content, of a polypeptide in accordance with the invention can be carried out by means of any method known to those skilled in the art.

By way of methods for detecting a polypeptide, mention may be made of Western blotting, slot blotting, dot blotting, ELISA (Enzyme Linked ImmunoSorbent Assay) methods of the singleplex or multiplex type, proteomics or glycomics methods, methods in which polypeptides in a polyacrylamide gel are stained with a silver-based stain, with Coomassie blue or with SYPRO, immunofluorescence methods, UV absorption methods, immunohistochemical methods in conventional, electron or confocal microscopy, FRET (fluorescence resonance energy transfer) methods, TR-FRET (time resolved FRET) methods, FLIM (fluorescence lifetime imaging microscopy) methods, FSPIM (fluorescence spectral imaging microscopy) methods, FRAP (fluorescence recovery after photobleaching) methods, reporter-gene methods, AFM (atomic force microscopy) methods, surface plasmon resonance methods, microcalorimetry methods, flow cytometry methods, biosensor methods, radioimmunoassay (RIA) methods, isoelectric focusing methods, and enzyme assays, methods using peptide chips, sugar chips, antibody chips, mass spectrometry methods, and SELDI-TOF spectrometry methods (Ciphergen).

More generally, enzyme immunoassay methods using protein solutions, which are more quantitative and sensitive, can in particular be used. These ELISA-type methods combine pairs of antibodies for capture and specific detection of the targeted antigen. Commercial antibodies or polyclonal, monoclonal or recombinant antibodies that have been specifically detected can be used. High-capacity multiplex ELISA techniques can also be used. Mention may thus be made of the multiplex approach such as antibodies on Luminex beads (for example, Bioplex from Bio-Rad), or antibodies on a flat surface (antibody arrays) (for example, the approach proposed by the company MesoScale Discovery).

In particular, it may be advantageous to detect the presence of a polypeptide in accordance with the invention by means of an antibody, where appropriate in a labelled form. Such an antibody can be labelled by means of a substance that is directly detectable or detectable by reaction with another reagent.

The term "antibody" is intended to denote, in general, monoclonal or polyclonal antibodies, and also immunoglobulin fragments capable of binding to an antigen and which can be produced by any genetic engineering technique known to those skilled in the art or by enzyme or chemical cleavage of an intact antibody.

An antibody capable of being used as a tool for evaluating a condition of an epidermis can be obtained by means of any method known to those skilled in the art, as described in "Antibodies: A Laboratory Manual", Cold Spring Harbor Laboratory Press, Cold Spring Harbor, N.Y. (1990).

According to another embodiment, a method for screening for biological or chemical compounds capable of modulating the biological activity of a polypeptide in accordance with the invention comprises at least the steps consisting in:

a) bringing at least one isolated polypeptide in accordance with the invention into contact with at least one chemical or biological compound to be tested, under conditions suitable for the manifestation of the biological activity of said polypeptide, b) carrying out a qualitative or quantitative measurement of said biological activity, and c) comparing said measurement to a reference measurement.

The screened biological or chemical compounds may be advantageously used for caring for the skin and its appendages.

A reference measurement can be obtained by repeating steps a) and b) in the absence of biological or chemical compounds to be tested.

According to one embodiment, an isolated polypeptide can be used in an acellular system, i.e. in a system which does not comprise cells but which reproduces cell functions, or in an isolated cell sample.

According to another embodiment, an acellular system can also be suitable for a method for screening for biological or chemical compounds or for physical treatments capable of modulating the expression of a nucleic acid sequence in accordance with the invention.

The term "biological activity" is intended to denote, in particular with regard to lacritin, a biological activity of the polypeptide represented by SEQ ID NO: 4, SEQ ID NO: 5 or SEQ ID NO: 10, optionally having undergone a glycosylation, and in particular a biological activity of syndecan-1-binding, mitogenic or anti-inflammatory type, of healing, of seborrhoea or sweating regulation, or of antimicrobial defence stimulation.

According to one embodiment, the biological activity of a polypeptide of the invention can in particular be its stimulatory activity on the proliferation and/or renewal of the terminal cells of the skin and/or of the hair follicle, and can be determined by any method known to those skilled in the art, for example on keratinocytes in culture.

According to one embodiment, the screening for a biological or chemical compound capable of modulating the biological activity of a polypeptide in accordance with the invention can be carried out by measuring the biological activity or the expression of a target molecule belonging to the signalling or metabolic pathways in which said polypeptide may be involved, such as, for example, a reporter-gene system.

Thus, a method of the invention concerns a method for screening for biological or chemical compounds capable of modulating the interaction, or binding, of a polypeptide in accordance with the invention with syndecan-1, comprising at least the steps consisting in:

a) bringing into contact at least one syndecan-1 molecule, at least one polypeptide in accordance with the invention and at least one chemical or biological compound to be tested, under conditions suitable for binding between said polypeptide and said syndecan-1 molecule, b) measuring the binding between said polypeptide and said syndecan-1 molecule, and c) comparing said measurement to a reference measurement.

The screened biological or chemical compounds may be advantageously used for caring for the skin and its appendages.

The reference measurement can be obtained by repeating steps a) and b) in the absence of compounds to be tested.

The interaction or the binding between a polypeptide of the invention and a syndecan-1 molecule can be carried out by any method known to those skilled in the art.

For example, the interaction or the binding between a polypeptide of the invention and a syndecan-1 molecule can be evaluated by measuring the polypeptide bound, relative to the total polypeptide used. In such a use, the syndecan-1 can be bound to a support and the polypeptide used can be labelled, for example with a radioisotope or a fluorescent label. After incubation of the labelled polypeptide in the presence of the syndecan-1 bound to a support and of the compound to be tested, the support is washed in order to remove the free polypeptide, and the polypeptide bound to the syndecan-1 is measured by detection of a radioactive or fluorescent signal, which can be quantified.

By way of a method suitable in particular for the invention, for detecting an interaction between two polypeptides, mention may be made of HTRF (Homogeneous time resolved fluorescence) or of SPR (Surface Plasmon Resonance), from Biacore.

The expression of the polypeptide or of the nucleic acid sequence, or the biological activity of the polypeptide, or its interaction with syndecan-1, may be unaffected by the compound or the treatment tested, or, on the other hand, may be inhibited or stimulated.

In the event of a stimulation of the expression, of the biological activity or of the interaction of the polypeptide with syndecan-1 being observed, the compound or the physical treatment tested is capable of being used for, for example, stimulating proliferation and/or renewal of the terminal cells of the skin and/or of the hair follicle, preventing and/or treating a skin and/or hair disorder, preventing and/or treating the cutaneous signs of ageing, in particular preventing and/or treating thinning of an epidermis and/or a loss of firmness, of elasticity, of density and/or of tonicity of an epidermis and/or the formation of wrinkles and fine lines, preventing and/or treating the cutaneous signs of dryness, in particular preventing and/or treating dehydration of the skin, preventing and/or treating skin disorders due to an imbalance in the barrier properties of the skin, stimulating the antimicrobial defences of the skin, promoting healing of the skin, stimulating sweating or sebaceous secretions of the skin and thus preventing and/or treating, respectively, a skin disorder associated with hypohidrosis or hyposeborrhoea.

In the event of an inhibition of the expression, of the biological activity or of the interaction of the polypeptide with syndecan-1 being observed, the compound or the physical treatment tested is capable of being used for, for example, reducing and/or inhibiting sebaceous secretions of the skin or sweating and thus preventing and/or treating, respectively, a skin disorder associated with hyperseborrhoea or with hyperhidrosis.

A method in accordance with the invention can be carried out on an isolated cell sample, an acellular sample or an isolated polypeptide, obtained either from a skin biopsy, or from cells in culture, in particular from an epidermal model, or from a surface skin sample of stratum corneum taken in particular by tape stripping or by simple washing, as described hereinafter.

Advantageously, by way of cell sample suitable for the invention, mention may be made of a sample of keratinocytes or of any other skin cell type expressing lacritin. Advantageously, a polypeptide used in a method according to the present invention may be lacritin.

Modulating Agent

For the purpose of the present invention, the expression "modulating agent" or "biological or chemical compound or physical treatment capable of modulating the expression and/or the biological activity of a polypeptide in accordance with the invention and/or its interaction with syndecan-1" is intended to mean any compound or physical phenomenon capable of acting, directly or indirectly, on at least one polypeptide in accordance with the invention, or a nucleic acid sequence encoding said polypeptide, or on an element of an intracellular or extracellular signalling pathway, or of a metabolic pathway, involving said polypeptide, or on an element involved in regulating the transcription and/or the translation of a nucleic acid sequence encoding said polypeptide.

For the purpose of the invention, the term "modulating", with regard to a given effect, is intended to mean the action of stimulating or inhibiting this effect, for the purposes in particular of conferring thereon a physiological intensity.

The biological or chemical compounds, or the physical treatments, derived from a screening method according to the invention, can be advantageously used for cosmetic or therapeutic purposes, in particular with regard to aesthetic or pathological skin or hair disorders.

Thus, the present invention advantageously makes it possible to screen for new active agents, i.e. biological or chemical compounds, for cosmetic care of the skin and its appendages, more particularly for stimulating proliferation and/or renewal of the terminal cells of the skin and/or of the hair follicle, preferably for preventing and/or treating a skin and/or hair disorder.

Advantageously, the invention makes it possible to screen for new cosmetic active agents for preventing and/or treating the cutaneous signs of ageing, in particular for preventing and/or treating thinning of an epidermis and/or a loss of firmness, of elasticity, of density and/or of tonicity of an epidermis and/or the formation of wrinkles and fine lines, for preventing and/or treating the cutaneous signs of dryness, in particular for preventing and/or treating dehydration of the skin, for preventing and/or treating skin disorders due to an imbalance in the barrier functions of the skin, in particular for stimulating the antimicrobial defences of the skin, for regulating sebaceous secretions of the skin, in particular for preventing and/or treating skin disorders associated with hyperseborrhoea or hyposeborrhoea, for regulating sweating, in particular for preventing and/or treating skin disorders associated with hypohidrosis or hyperhidrosis, and for stimulating the growth of body hairs and of the hair.

The present invention advantageously makes it possible to screen for new active agents, i.e. biological or chemical compounds, for therapeutic care of the skin and its appendages, more particularly for promoting healing of the skin.

According to one embodiment, a biological or chemical modulating agent suitable for the invention may be an agent that stimulates the activity, the stability or the expression of said polypeptide, or its interaction with syndecan-1.

In particular, a modulating agent may be a stimulating agent such as the mixture composed of a *Bifidobacterium longum* lysate and of phytosphingosine-salicylate.

Such a mixture may in particular be a composition comprising a serum composed of 10% of *Bifidobacterium longum* lysate (Bifidiobiotic complex CLR) and 0.002% of phytosphingosine-SLC.

According to another embodiment, a biological or chemical modulating agent suitable for the invention may be an agent that inhibits the activity, the stability or the expression of said polypeptide, or its interaction with syndecan-1.

In particular a modulating agent may be an inhibiting agent chosen from peptides or peptidomimetics derived from lacritin, proteases or activators of proteolysis of lacritin, peptide or nucleotide aptamers and interfering RNAs.

Among the peptides or peptidomimetics, at least one of the sequences chosen from SEQ ID NO: 7, SEQ ID NO: 8, SEQ ID NO: 9 or SEQ ID NO: 10 are more particularly considered.

According to one embodiment, a modulating agent of the invention is not a *Bifidobacterium longum* lysate not associated with a phytosphingosine-salicylate.

According to another embodiment, a modulating agent of the invention is not a phytosphingosine-salicylate not associated with a *Bifidobacterium longum* lysate.

According to one embodiment, a modulating agent in accordance with the invention is not a *Bifidobacterium longum* lysate associated with an anti-pollution agent or an agent exhibiting irritation effect. In particular a modulating agent in accordance with the invention is not a *Bifidobacterium longum* lysate associated with ellagic acid or phenoxyethanol.

According to another embodiment, a modulating agent in accordance with the invention is not a *Bifidobacterium longum* lysate associated with vitamin E, ascorbic acid or a salt of ascorbic acid, such as calcium ascorbate or magnesium ascorbate, a black currant seed oil, a *Vitreoscilla filiformis* extract, an antioxidant, a plant extracellular matrix.

According to another embodiment, a modulating agent in accordance with the invention is not a phytosphingosine-salicylate associated with a brown algae extract *Padina pavonica*.

According to another preferred embodiment, a modulating agent in accordance with the invention is not a black thea extract, biotin, a *Thermus thermophilus* ferment, a lactic acid bacterium, and in particular *Streptococcus thermophilus*.

According to a preferred embodiment, an modulating agent according to the invention is not a siRNA of the syndecan-1.

Compositions

A subject of the present invention is the use of an effective amount of at least one polypeptide of amino acid sequence represented by SEQ ID NO: 4, an analogue thereof or a fragment thereof, of at least one nucleic acid sequence encoding this polypeptide, or of at least one agent that modulates the activity, the stability or the expression of this polypeptide, or its interaction with syndecan-1, as an agent that is of use in caring for the skin and its appendages.

Advantageously, such polypeptides, nucleic acid sequences or modulating agents can be used in a cosmetic composition.

According to another embodiment, a subject of the present invention is the use of an effective amount of at least one polypeptide of amino acid sequence represented by SEQ ID NO: 4, an analogue thereof or a fragment thereof, of at least one nucleic acid sequence encoding this polypeptide, or of at least one agent that modulates the activity, the stability or the expression of this polypeptide, or its interaction with syndecan-1, for the preparation of a therapeutic composition for caring for the skin and its appendages.

The cosmetic and therapeutic compositions of the invention are more particularly devoted to the prevention and/or treatment of conditions of the skin, or of conditions of the hair follicles, of body hairs or of the hair as defined above.

It is understood that all the cosmetic or therapeutic compositions under consideration according to the invention use a physiologically acceptable medium.

For the purpose of the present invention, the term "physiologically acceptable medium" is intended to denote a medium suitable for the application of a composition to the skin, the scalp, the lips and keratin fibres such as the hair, the nails and body hairs, or, as appropriate, orally or parenterally.

In general, any composition of the invention can be applied to the skin, in particular to any area of the skin of the body, or its appendages, in particular body hairs and the hair.

A cosmetic composition according to the invention may contain adjuvants that are common in the cosmetics field, such as hydrophilic or lipophilic gelling agents, hydrophilic or lipophilic additives, preservatives, antioxidants, solvents, fragrances, fillers, screening agents, odour absorbers and dyestuffs.

The amounts of the various constituents of the compositions according to the invention are those conventionally used in the fields under consideration.

The amount of chemical or biological compound, of polypeptide, of nucleic acid sequence or of modulating agent in accordance with the invention, contained in a composition according to the invention, also referred to as "effective amount", depends, of course, on the nature of the compound and on the desired effect and can therefore vary to a large extent.

To give an order of magnitude, a composition can contain a modulating agent in accordance with the invention or a polypeptide in an amount representing from 0.00001% to 50% of the total weight of the composition, in particular in an amount representing from 0.001% to 10% of the total weight of the composition, and more particularly in an amount representing from 0.1% to 1% of the total weight of the composition.

According to another embodiment, a cosmetic or therapeutic composition in accordance with the invention may also comprise at least one additional cosmetic and/or therapeutic active agent.

Additional Active Agents

As examples of additional active agents that can be used in the context of the present invention, mention may be made of cosmetic oils, such as silicone oils, plants oils of triglyceride type, hydrocarbon-based oils such as Parleam oil, and esters of fatty acids and of fatty alcohols.

It may also be possible to use other active agents which make it possible to improve the condition of the skin and/or its appendages, such as hydrating or moisturizing active agents or active agents which make it possible to improve the natural lipid barrier, such as ceramides, cholesterol sulphates and/or fatty acids, and mixtures thereof.

It may also be possible to use enzymes which have an activity on the skin and/or its appendages, such as proteases, lipases, glucosidases, amidases, cerebrosidases and/or melanases, and mixtures thereof.

Other examples of active agents suitable for implementing the present invention include: analgesic active agents, anti-yeast active agents, antibacterial active agents, antiparasitic active agents, antifungal active agents, antiviral active agents, steroidal anti-inflammatory active agents, anaesthetic active agents, antipruritic active agents, keratolytic active agents, free-radical scavenger active agents, anti-seborrhoeic active agents, antidandruff active agents, anti-acne active agents, active agents intended for preventing ageing of the skin and/or for improving the condition thereof, anti-dermatitis active agents, anti-irritant active agents, immuno-modulatory active agents, active agents for the treatment of dry skin, antiperspirant active agents, antipsoriatic active agents, active agents for protecting against UV radiation, antihistamine active agents, healing active agents, self-tanning active agents, antioxidants such as green tea or active fractions thereof, glycerol, laponite, caffeine, aromatic essential oils, colorants, depigmenting active agents, liporegulators, emollient, refreshing, deodorizing, desensitizing, bleaching or nourishing active agents, active agents for reducing skin differentiation and/or proliferation and/or cutaneous pigmentation, and mixtures thereof.

Evaluation of the Condition of an Epidermis

According to another aspect, the present invention also relates to the use of at least one polypeptide in accordance with the invention or of at least one nucleic acid sequence encoding said polypeptide, as a tool for in vitro or ex vivo characterization of a condition of the skin.

The conditions of the skin under consideration in the invention are in particular as defined above.

By way of example, it is possible to characterize according to the invention a condition of the skin chosen from skin dryness, such as xerosis, skin ageing, in particular chronological and/or photoinduced ageing, oily skin, skin atopy, atopic dermatitis, alopecia or alopecia greata, ichthyosis, psoriasis, rosacea, lichen, acne, seborrhoeic dermatitis, palmoplantar keratoderma, or malignant or benign neoplasia.

Preferably, the use makes it possible to characterize a condition of the skin chosen from skin dryness or chronological and/or photoinduced skin ageing.

According to one embodiment, a method for characterizing a condition of the skin comprises at least the steps consisting in:

a) carrying out, in a sample isolated from said skin, a qualitative or quantitative measurement of a polypeptide in accordance with the invention, or of a nucleic acid sequence encoding said polypeptide, and b) comparing said measurement carried out in step a) to a reference measurement.

A reference measurement may be obtained from a sample of skin described as normal from the physiological point of view, such as young and normally hydrated skin. The observation of a deviation between the reference measurement and the test measurement, in particular the measurement in step a), may be an indicator of a possible skin disorder which can be corrected by using compounds of the invention.

A method of the invention advantageously makes it possible to characterize a condition of the skin as defined above, and in particular chosen from skin dryness or chronological and/or photoinduced skin ageing.

According to another of its aspects, the present invention relates to the use of at least one polypeptide in accordance with the invention, or of at least one nucleic acid sequence encoding said polypeptide, for characterizing the effectiveness of a cosmetic treatment for caring for the skin and its appendages, in particular for characterizing the effectiveness of a treatment for a skin disorder as defined above.

Preferably, the use of the invention makes it possible to characterize the effectiveness of a cosmetic treatment for a skin disorder in particular chosen from skin dryness or chronological and/or photoinduced skin ageing.

The present invention also relates to a cosmetic, or alternatively nontherapeutic, method for demonstrating an effect of a cosmetic treatment capable of causing a skin disorder to diminish in an individual, comprising at least the steps consisting in:

a) carrying out, before the cosmetic treatment or method is implemented, at least one first measurement, in a first sample of epidermis taken from said individual, of a biological activity and/or of the expression of a polypeptide in accordance with the invention, or of the expression of a nucleic acid sequence encoding said polypeptide, b) carrying out, after the cosmetic treatment or method has been implemented, at least one second measurement, in a second sample of epidermis taken from said individual, of said biological activity and/or of said expression of said polypeptide or of said expression of said nucleic acid sequence, determined in step a), and c) comparing the first and second measurements, in particular in order to deduce therefrom a piece of information relating to at least one effect of the implementation of the cosmetic treatment.

The measurements carried out in steps a) and/or b) of the methods above can be carried out by means of any method known to those skilled in the art and, for example, according to one of the methods previously described.

Preferably, the method of the invention makes it possible to demonstrate an effect of a cosmetic treatment capable of causing a skin disorder to diminish, said skin disorder being as defined above, in particular chosen from skin dryness or chronological and/or photoinduced skin ageing.

The methods of the invention are particularly advantageous insofar as their implementation does not require recourse to an invasive technique. A sample of epidermis can thus be obtained by "stripping" techniques and directly analysed by a conventional analytical technique, in particular as described above.

These strippings are sticky surfaces applied to the surface of the epidermis, such as Blenderm® from 3M, D'squam (commercial adhesive from CuDERM), cyanoacrylate glue or the varnish stripping method. By virtue of these strippings, the adherent corneocytes and the content of their intercellular spaces can be sampled and subsequently subjected to an extraction which makes it possible to access the protein content.

The taking of a sample suitable for a method of the invention may also be carried out more directly by "washing" the skin surface by means, for example, of accessories of the vane turbine type, of the spiral cell type (as described in patent FR 2 667 778) combined with a fluid circuit, or simply by addition/removal of a drop of buffer at the surface of the skin.

By way of indication, other sampling methods suitable for implementing the invention may be mentioned, such as methods based on scraping the upper part of the stratum corneum by means of a twin blade system. This technique makes it possible to collect squamae which can then be directly analysed by various techniques in order to determine the mineral, amino acid or lipid contents.

A method according to the invention may also be carried out on a sample of epidermis taken from an epidermis cell model, or from a reconstructed isolated skin in order to define the condition thereof.

As indicated above, the uses and methods of the invention are advantageously carried out in vitro or ex vivo. However, these uses or methods can also be carried out in vivo on nonhuman mammals or on humans, in particular through clinical trials, in order, for example, to evaluate the clinical efficacy or the innocuousness of various skin disorder treatments, for example as defined above.

According to another aspect, the present invention relates to a method for cosmetic treatment of a skin disorder, comprising at least one step consisting in applying at least one cosmetic composition in accordance with the invention to at least one part of the skin, the body hairs and/or the hair.

Advantageously, a method of the invention makes it possible to treat a skin disorder as defined above, and in particular chosen from skin dryness or chronological and/or photoinduced skin ageing.

According to another aspect, the present invention relates to the use of an effective amount of at least one polypeptide in accordance with the invention or of at least one nucleic acid sequence encoding said polypeptide, of at least one agent that modulates the activity, the stability or the expression of said polypeptide or of said nucleic acid sequence, or the interaction of said polypeptide with syndecan-1, for preparing and/or improving a pluristratified epithelial cell model, in particular of epidermal or mucosal type, and in particular a reconstructed skin model.

There is a great advantage to developing organotypic models that are as close as possible to in-vivo conditions, for evaluating security and efficacy of active agents and formulations with cosmetic and dermatological applications.

The use of lacritin in a culture medium is capable of improving the quality of the models developed.

According to another aspect, the present invention relates to a method for preparing an isolated reconstructed skin, comprising at least the step of bringing at least an effective amount of at least one polypeptide in accordance with the invention or of at least one nucleic acid sequence encoding said polypeptide, or of at least one agent that modulates the activity, the stability or the expression of said polypeptide or of said nucleic acid sequence, or the interaction of said polypeptide with syndecan-1, into contact with cells capable of generating an isolated reconstructed skin, and in particular keratinocytes.

For the purpose of the invention, the term "reconstructed skin model" is intended to denote a model in which various cell types, such as, in particular, the natural constituents of the skin, like, for example, keratinocytes, fibroblasts, Langerhans cells and melanocytes, are combined. The fibroblast cells may optionally be irradiated.

Such models and the preparation thereof are known to those skilled in the art.

For the purpose of the present invention, "one" should be understood, unless otherwise indicated, to mean "at least one".

The examples and figures hereinafter are given by way of nonlimiting illustration of the invention.

FIGURES

FIG. 1: represents the nucleic acid sequences SEQ ID NO: 1, SEQ ID NO: 2 and SEQ ID NO: 3.

FIG. 2: represents the amino acid sequences SEQ ID NO: 4, SEQ ID NO: 5, SEQ ID NO: 6, SEQ ID NO: 7, SEQ ID NO: 8, SEQ ID NO: 9 and SEQ ID NO: 10.

EXAMPLE 1

Demonstration of the Expression of Lacritin in the Skin a) Protocol

In-vivo varnish stripping samples are taken, according to the protocol described in Mehul et al. J Biol Chem., 2000, 275(17):12841-7, from the two forearms (posterior face), over a surface area of 90 cm$^2$, of two groups of individuals:

1) Young skin group: 30-40 years old, 20 individuals, dry skin;

2) Aged skin group: 60-65 years old, 20 individuals, dry skin.

These skin specimens (stratum corneum varnish stripping) are then analysed by proteomics by means of a "isobaric labelling" technique, in order to evaluate the expression of various proteins between aged skin versus young skin.

This "isobaric labelling" technique or iTRAQ™ is based on the labelling of tryptic peptides with a series of reagents, which are termed isobaric since they all have a molecular mass of 145 Da and form a covalent bond with the primary amines of the amino-terminal end of the side chain of lysine residues.

The labelled peptides are detected by mass spectrometry with the intrinsic mass of the peptide+145 Da, originating from the reagent. At the peptide fragmentation stage, the contribution of each of the reagents is assessed by the release of ions (fragments) having specific different masses.

Such a method is described in detail by Zieske (J. Exp. Bot., 2006, 57:1501) or Wiese et al. (Proteomics, 2007, 7: 340).

The protocol used, namely the iTRAQ Reagents Multiplex kit (4352135), from Applied Biosystems, was employed in accordance with the manufacturer's instructions.

The expression of the proteins of the samples taken is evaluated by means of two iTRAQ studies carried out in parallel.

b) Results

A differential proteomics analysis based on the peptides of amino acid sequences represented by SEQ ID NO: 7, SEQ ID NO: 8 and SEQ ID NO: 9 show that human lacritin (uniprotKB/swissprot: Q9GZZ8 or SEQ ID NO: 4) is identified for all the samples described above. Aged skin/dry skin ratios are thus determined and the results of quantification for lacritin indicate a mean aged/young ratio equal to 0.38 (standard deviation=0.33), which proves that lacritin is not only expressed in the stratum corneum of a human epidermis, but that it is, in addition, predominantly expressed in the young skin group and has a tendency to be underexpressed with age.

Therefore, in view of these results, it is possible to take advantage of lacritin as a novel marker for a condition of the skin, in particular of aged skin.

EXAMPLE 2

Evaluation of the Effect of a Composition Containing 10% of *Bifidobacterium longum* Lysate and 0.002% of Phytosphingosine SLC on the Level of Lacritin Expression a) Protocol The present study relates to varnish stripping samples, taken as described in Mehul et al., J. Biol Chem., 2000, 275(17): 12841-7, over a surface area of 90 cm$^2$ from the forearm, posterior face, of 24 female individuals between the ages of 40 and 45, and having a "dry skin" characteristic.

16 of these individuals are treated topically on just one of the two arms, twice a day, in the morning and the evening, for 56 days, i.e. 2 months, with a cosmetic composition characterized by a serum composed of 10% of *Bifidobacterium longum* lysate (Bifidiobiotic complex CIA) and 0.002% of phytosphingosine-SLC.

Among the individuals tested with the cosmetic composition, each one is her own control since both arms are sampled but only one arm is treated.

Complex CLR is a lysate registered under the INCI name: Bifidat ferment Lysate, under the EINECS name: *Bifidobacterium longum*, under EINECS No.: 306-168-4, and under CAS No.: 96507-89-0.

Such a lysate is in particular sold under the name Repair Complex CLR® by the company K. Richter GmbH.

The phytosphingosine-salicylate derivative is the product sold by the company Evonick Goldschmidt under the name Phytosphingosine SLC®.

Samples are thus taken at D0 and D56 from each of the 24 individuals, thus making it possible to compare four conditions, namely D0, D56, "untreated" individuals and "treated" individuals.

The lacritin present in these samples is then quantified by means of a differential proteomics analysis as described in Example 1.

b) Results

For each "treated" and "untreated" individuals condition, a mean of the D56/D0 ratios is obtained, thus making it possible to evaluate the effect of the treatment associated with the cosmetic product.

The D56/D0 ratios are calculated according to the following formula:

$$\% \text{ effect of the treatment} = 100 \times \frac{\text{treated } D56/D0 \text{ ratio} - \text{untreated } D56/D0 \text{ ratio}}{\text{untreated } D56/D0 \text{ ratio}}$$

The comparison of the means of the D56/D0 ratios of the "treated" and "untreated" individuals shows an increase in lacritin expression in the "treated" individuals of 491%±220 after 2 months of topical treatment with the composition tested.

This study, which attests to the lacritin expression-stimulating properties of said composition, therefore made it possible to demonstrate that lacritin is actually a tool for screening for biological or chemical compounds, and, in addition, an effective tool for characterizing the effectiveness of a cosmetic treatment for caring for the skin and its appendages.

The invention claimed is:

1. A method for characterizing a condition of skin, said method comprising the steps of:
   a) performing, in a first sample isolated from said skin, a quantitative measurement of at least one polypeptide of amino acid sequence represented by SEQ ID NO: 4, or a nucleic acid sequence encoding said at least one polypeptide; and
   b) comparing said measurement to a reference measurement, wherein the reference measurement is obtained from a quantitative measurement of the polypeptide, or of the nucleic acid sequence encoding the polypeptide, of a second sample taken from reference skin distinct from the skin of the first sample, the quantitative measurements being made by means of an isobaric labeling technique, said condition of the skin being chosen from skin dryness and chronological and/or photoinduced skin ageing.

2. The method of claim 1, wherein the second sample is from skin that is younger than the first sample and/or is devoid of dryness.

* * * * *

SEQUENCE LISTING

<160> NUMBER OF SEQ ID NOS: 10

<210> SEQ ID NO 1
<211> LENGTH: 417
<212> TYPE: DNA
<213> ORGANISM: Homo sapiens

<400> SEQUENCE: 1

```
atgaaattta ccactctcct cttcttggca gctgtagcag gggccctggt ctatgctgaa      60
gatgcctcct ctgactcgac gggtgctgat cctgcccagg aagctgggac tctaagcct     120
aatgaagaga tctcaggtcc agcagaacca gcttcacccc cagagacaac cacaacagcc    180
caggagactt cggcggcagc agttcagggg acagccaagg tcacctcaag caggcaggaa    240
ctaaaccccc tgaaatccat agtggagaaa agtatcttac taacagaaca agcccttgca    300
aaagcaggaa aaggaatgca cggaggcgtg ccaggtggaa aacaattcat cgaaaatgga    360
agtgaatttg cacaaaaatt actgaagaaa ttcagtctat taaaaccatg ggcatga       417
```

<210> SEQ ID NO 2
<211> LENGTH: 360
<212> TYPE: DNA
<213> ORGANISM: Homo sapiens

<400> SEQUENCE: 2

```
gaagatgcct cctctgactc gacgggtgct gatcctgccc aggaagctgg gacctctaag     60
cctaatgaag agatctcagg tccagcagaa ccagcttcac ccccagagac aaccacaaca    120
gcccaggaga cttcggcggc agcagttcag gggacagcca aggtcacctc aagcaggcag    180
gaactaaacc ccctgaaatc catagtggag aaaagtatct tactaacaga acaagccctt    240
gcaaaagcag gaaaaggaat gcacggaggc gtgccaggtg gaaaacaatt catcgaaaat    300
ggaagtgaat ttgcacaaaa attactgaag aaattcagtc tattaaaacc atgggcatga    360
```

<210> SEQ ID NO 3
<211> LENGTH: 57
<212> TYPE: DNA
<213> ORGANISM: Homo sapiens

<400> SEQUENCE: 3

```
atgaaattta ccactctcct cttcttggca gctgtagcag gggccctggt ctatgct        57
```

<210> SEQ ID NO 4
<211> LENGTH: 138
<212> TYPE: PRT
<213> ORGANISM: Homo sapiens

<400> SEQUENCE: 4

```
Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Ala Gln Glu Thr Ser
    50                  55                  60

Ala Ala Ala Val Gln Gly Thr Ala Lys Val Thr Ser Ser Arg Gln Glu
65                  70                  75                  80
```

```
Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135
```

<210> SEQ ID NO 5
<211> LENGTH: 119
<212> TYPE: PRT
<213> ORGANISM: Homo sapiens

<400> SEQUENCE: 5

```
Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
            20                  25                  30

Ser Pro Pro Glu Thr Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Val Pro Gly Gly Lys Gln
                85                  90                  95

Phe Ile Glu Asn Gly Ser Glu Phe Ala Gln Lys Leu Leu Lys Lys Phe
            100                 105                 110

Ser Leu Leu Lys Pro Trp Ala
        115
```

<210> SEQ ID NO 6
<211> LENGTH: 19
<212> TYPE: PRT
<213> ORGANISM: Homo sapiens

<400> SEQUENCE: 6

```
Met Lys Phe Thr Thr Leu Leu Phe Leu Ala Ala Val Ala Gly Ala Leu
1               5                   10                  15

Val Tyr Ala
```

<210> SEQ ID NO 7
<211> LENGTH: 11
<212> TYPE: PRT
<213> ORGANISM: Homo sapiens

<400> SEQUENCE: 7

```
Ser Ile Leu Leu Thr Glu Gln Ala Leu Ala Lys
1               5                   10
```

<210> SEQ ID NO 8
<211> LENGTH: 12
<212> TYPE: PRT
<213> ORGANISM: Homo sapiens

<400> SEQUENCE: 8

```
Gln Phe Ile Glu Asn Gly Ser Glu Phe Ala Gln Lys
1               5                   10
```

```
<210> SEQ ID NO 9
<211> LENGTH: 9
<212> TYPE: PRT
<213> ORGANISM: Homo sapiens

<400> SEQUENCE: 9

Lys Phe Ser Leu Leu Lys Pro Trp Ala
1               5

<210> SEQ ID NO 10
<211> LENGTH: 21
<212> TYPE: PRT
<213> ORGANISM: Homo sapiens

<400> SEQUENCE: 10

Gly Lys Gln Phe Ile Glu Asn Gly Ser Glu Phe Ala Gln Lys Leu Leu
1               5                   10                  15

Lys Lys Phe Ser Leu
            20
```